(12) United States Patent
Rudnic et al.

(10) Patent No.: US 6,514,532 B2
(45) Date of Patent: Feb. 4, 2003

(54) SOLUBLE FORM OSMOTIC DOSE DELIVERY SYSTEM

(75) Inventors: Edward M. Rudnic, North Potomac, MD (US); Beth A. Burnside, Bethesda, MD (US); Henry H. Flanner, Montgomery, MD (US); Sandra E. Wassink, Frederick, MD (US); Richard A. Couch, Chevy Chase, MD (US); Jill E. Pinkett, Baltimore, MD (US)

(73) Assignee: Shire Laboratories, Inc., Rockville, MD (US)

( * ) Notice: Subject to any disclaimer, the term of this patent is extended or adjusted under 35 U.S.C. 154(b) by 0 days.

(21) Appl. No.: 10/035,077

(22) Filed: Dec. 28, 2001

(65) Prior Publication Data

US 2002/0102306 A1 Aug. 1, 2002

Related U.S. Application Data

(63) Continuation of application No. 09/634,224, filed on Aug. 9, 2000, now Pat. No. 6,361,796, which is a continuation-in-part of application No. 08/954,947, filed on Oct. 22, 1997, now Pat. No. 6,110,498.

(60) Provisional application No. 60/029,032, filed on Oct. 25, 1996.

(51) Int. Cl.[7] .......................... A61K 9/24; A61K 9/28; A61K 9/42; A61K 9/36; A61K 9/32
(52) U.S. Cl. ...................... 424/473; 424/474; 424/476; 424/479; 424/480; 424/482; 514/960
(58) Field of Search ................................ 424/400, 464, 424/465, 472, 473, 474, 476, 479, 480, 482; 514/960

Primary Examiner—Jose' G. Dees
Assistant Examiner—Sharmila S Gollamudi
(74) Attorney, Agent, or Firm—Elliot M. Olstein

(57) ABSTRACT

Disclosed is an osmotic pharmaceutical delivery system comprising (a) a semi-permeable wall that maintains its integrity during pharmaceutical delivery and which has at least one passage therethrough; b) a single, homogeneous composition within said wall, which composition consists essentially of (i) a pharmaceutically active agent, (ii) at least one non-swelling solubilizing agent which enhances the solubility of the pharmaceutically active agent; (iii) at least one non-swelling osmotic agent and (iv) a non-swelling wicking agent dispersed throughout the composition which enhances the surface area contact of the pharmaceutical agent with the incoming aqueous fluid.

15 Claims, 7 Drawing Sheets

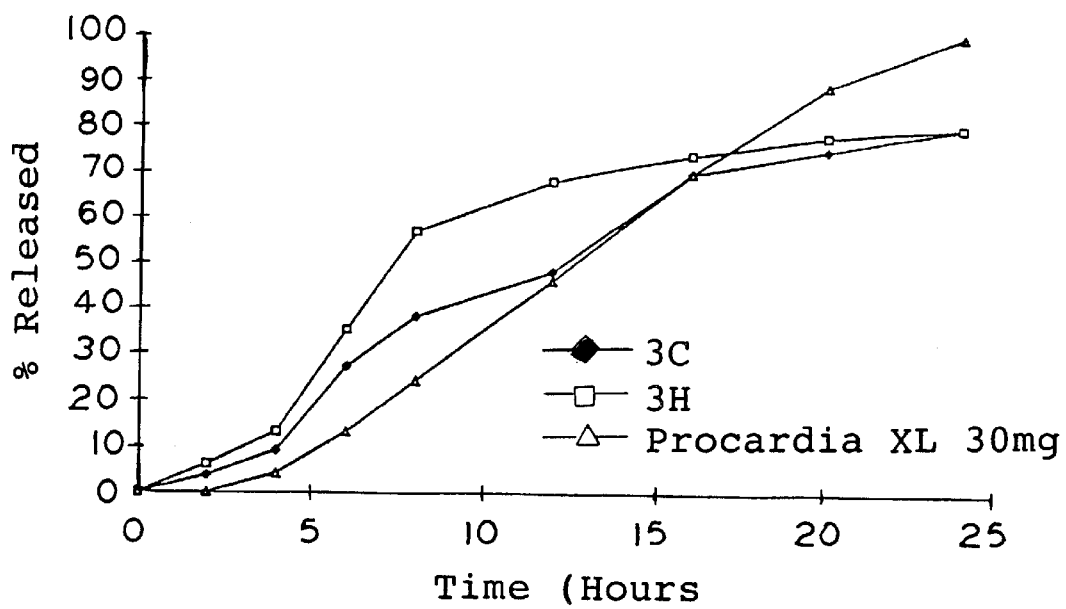
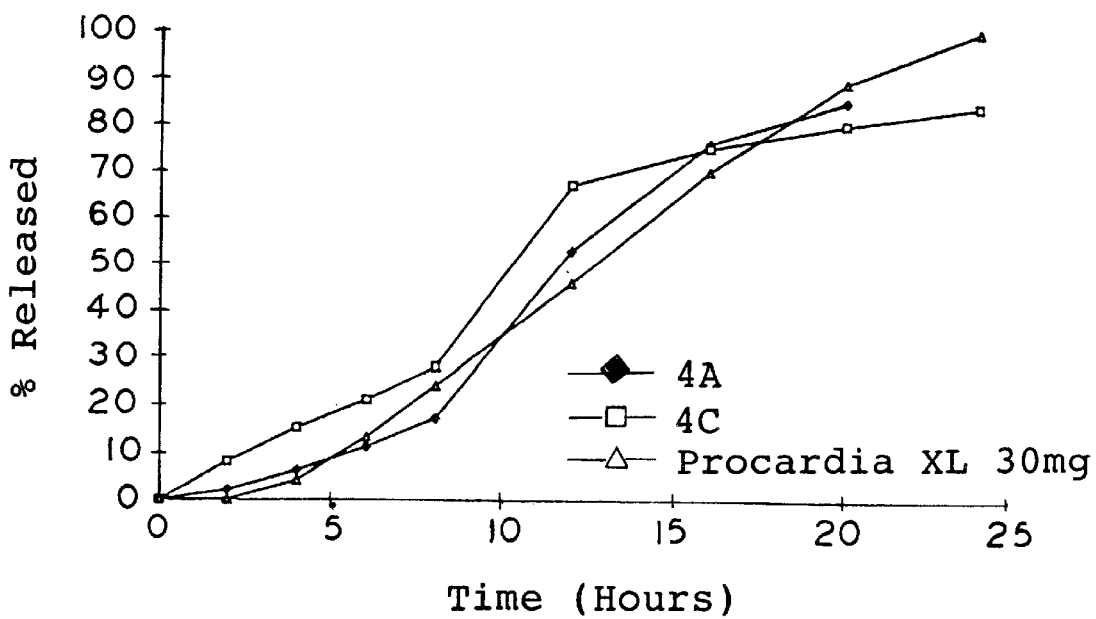
FIG. 6

SOLUBLE FORM OSMOTIC DOSE DELIVERY SYSTEM

This application is a continuation application Ser. No. 09/634,224, filed on Aug. 9, 2000, now U.S. Pat. No. 6,361,796, which is a continuation-in-part of application Ser. No. 08/954,947, filed Oct. 22, 1997 now U.S. Pat. No 6,110,498, which is a continuation-in-part of U.S. provisional application Serial No. 60/029,032, filed Oct. 25, 1996.

The present invention relates to the field of osmotic pharmaceutical dose delivery systems and preparations, particularly preparations which can be administered orally.

Theeuwes et al., U.S. Pat. No. 3,916,899, discloses a drug delivery preparation that is said to release the pharmaceutical agent through openings in the wall of the tablet or capsule by the osmotic pressure differential that is set up between the concentration of pharmaceutical agent in the tablet or capsule interior and the exterior fluid environment of the patient when the medicament is taken orally. See, also, Theeuwes et al., U.S. Pat. No. 3,845,770 which discloses another preparation for osmotic pressure differential delivery of a pharmaceutical agent. In this original type of approach the interior of the tablet had a hydrophobic core surrounded by a hydrophilic layer within the tablet wall. As such, water entering the tablet remained in the hydrophilic layer and so very little drug was actually released.

It has been believed that this approach did not deliver the pharmaceutical agent as completely or efficiently as had previously been thought. Therefore, a different approach to releasing the pharmaceutical agent was developed. In this approach the interior of the tablet or capsule is characteristically of two layers, one containing the pharmaceutical agent (again to be released through openings in the wall of the tablet or capsule) and the other being a layer of material that swells when coming into contact with water. These materials that swell or expand to an equilibrium state when exposed to water or other biological fluids are referred to as "osmopolymers". This volume expansion is used to physically force the pharmaceutical agent out through openings which have been formed in the wall, shell or coating during manufacture. The pharmaceutical agent is primarily released as insoluble particles, which therefore have limited bioavailability. This has commonly been referred to as the "push/pull" approach. See, for example, U.S. Pat. Nos. 5,422,123; 4,783,337; 4,765,989; 4,612,008; and 4,327,725. The patent literature has taught that this approach was necessary to deliver adequate doses, at controlled rates and for extended times, of a broad variety of drugs. Other "osmotic delivery systems have also been described. See, for example, U.S. Pat. Nos. 4,609,374; 4,036,228; 4,992,278; 4,160,020; and 4,615,698. The osmopolymers used in these types of systems are components whose functions are to swell when they interact with water and aqueous fluids. This swelling effect is defined in these patents as a property of embibing fluid so is to expand to a very high degree, usually exhibiting a 2 to 50 fold volume increase.

SUMMARY OF THE INVENTION

In arriving at the present invention it has been discovered that it is possible to efficiently deliver therapeutically effective doses, at controlled rates and for extended times, of a broad variety of drugs without the need for polymers that swell or expand within the tablet wall so as to physically force the medicament particles out into their intended environment of use. As used herein the term "swell", i.e. that property which the present invention has been able to avoid, is used so as to have the same definition as in the patents described above. Further, the invention makes it possible to deliver agents which have limited aqueous solubility.

In accordance with the preferred invention, there is provided an osmotic delivery system, preferably in the form of a tablet, which dispenses a therapeutic agent having a limited solubility in water or physiological environments without the use of osmopolymers or swelling agents to deliver the therapeutic agents. Further in accordance with the present invention, the therapeutic agent is incorporated into a composition which is capable of solubilizing the therapeutic agent whereby the therapeutic agent is delivered in a predominantly solubilized form.

In a preferred embodiment, the invention has combined appropriate solubilizing agents and, throughout the composition containing the solubilizing and pharmaceutical agent (s), a "wicking" agent which provides enhanced flow channels for the pharmaceutical agent which has been made predominantly into its solubilized form by the solubilizing agent(s) while still within the tablet or capsule. Thus, the drug is delivered out through passages in the coating wall by true osmosis predominantly in its solubilized form, rather than by physical force on a particulate form.

Accordingly, in one aspect, the invention provides an osmotic pharmaceutical delivery system comprising (a) a semi-permeable wall that maintains its integrity during pharmaceutical delivery and which has at least one passage therethrough; (b) a single, homogeneous composition within said wall, which composition contains (i) a pharmaceutically active agent, (ii) at least one non-swelling solubilizing agent which enhances the solubility of the pharmaceutically active agent; (iii) at least one non-swelling osmotic agent and (iv) a non-swelling wicking agent dispersed throughout the composition which enhances the surface area contact of the pharmaceutical agent with the incoming aqueous fluid. The pharmaceutical agent is thus released in a predominantly soluble form.

Preferred non-swelling solubilizing agents include (i) agents that inhibit crystal formation of the pharmaceutical or otherwise acts by complexation therewith; (ii) a high HLB (hydrophilic-lipophilic balance) micelle-forming surfactant, particularly non-ionic and/or anionic surfactants; (iii) citrate esters; and combinations thereof, particularly combinations of complexation agents with anionic surfactants. Preferred non-swelling osmotic agents include sugars with ten or fewer rings, preferably five or fewer rings and most preferably two rings. Examples include fructose, lactose, xylitol and sorbitol. Preferred wicking agents include colloidal silicon dioxide and polyvinyl pyrrolidone and sodium lauryl sulfate can also function as wicking agents.

BRIEF DESCRIPTION OF THE DRAWINGS

The invention will now be further described by reference to a brief description of each of the accompanying drawings. The brief description and the drawings are in no way a limitation of the invention.

FIG. 5 diagrammatically shows the percent of nifedipine released by dosage forms of the invention containing formulations 3C (30 mg); 3H (30 mg); as shown on Table 3 as compared to Procardia XL®(Pfizer, Inc.; 30 mg).

FIG. 6 diagrammatically shows the percent of nifedipine released by forms of the invention containing formulations 4H (30 mg); 4C (90 mg); as shown on Table 4 as compared to Procardia XL®(Pfizer, Inc.; 30 mg).

DETAILED DESCRIPTION OF PREFERRED EMBODIMENTS

Figure 1A:
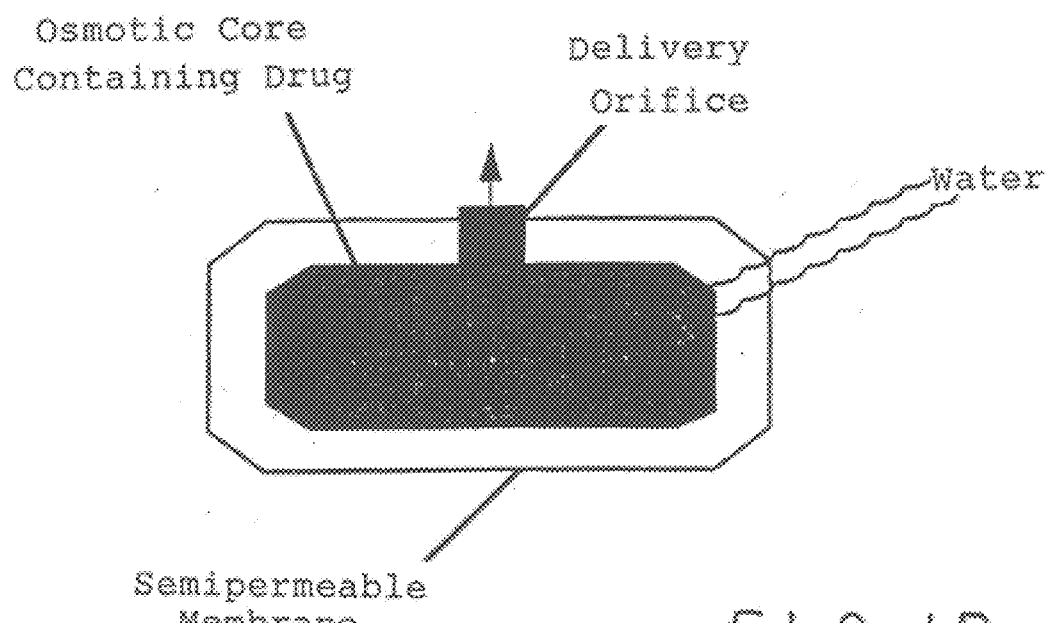
FIG. 1A schematically illustrates the elementary osmotic dose delivery system of the prior art.
Figure 1B:
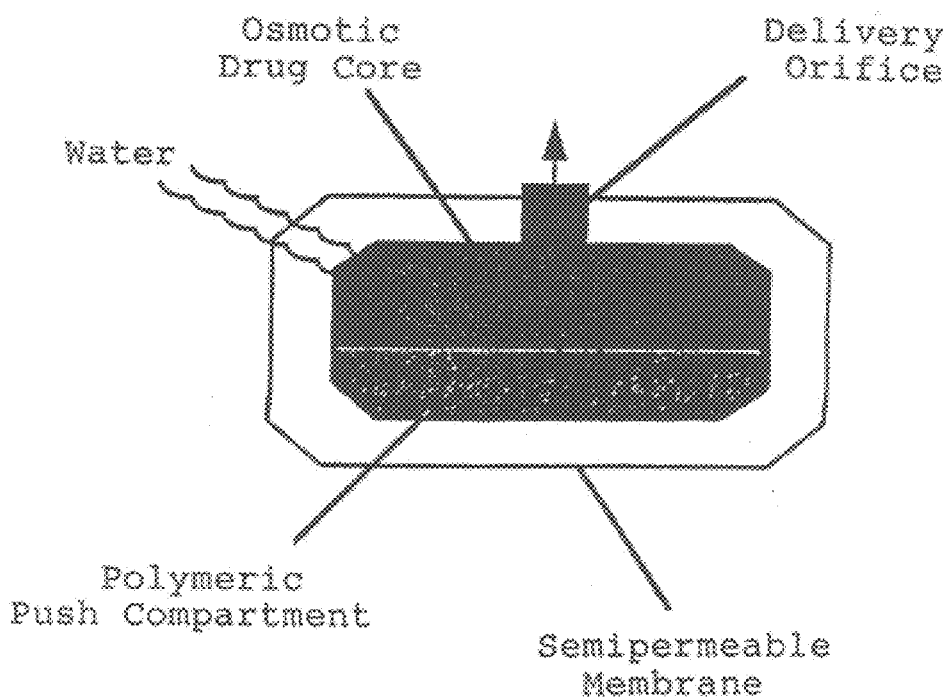
FIG. 1B schematically illustrates the osmotic dose delivery system of the prior art.
Figure 2:
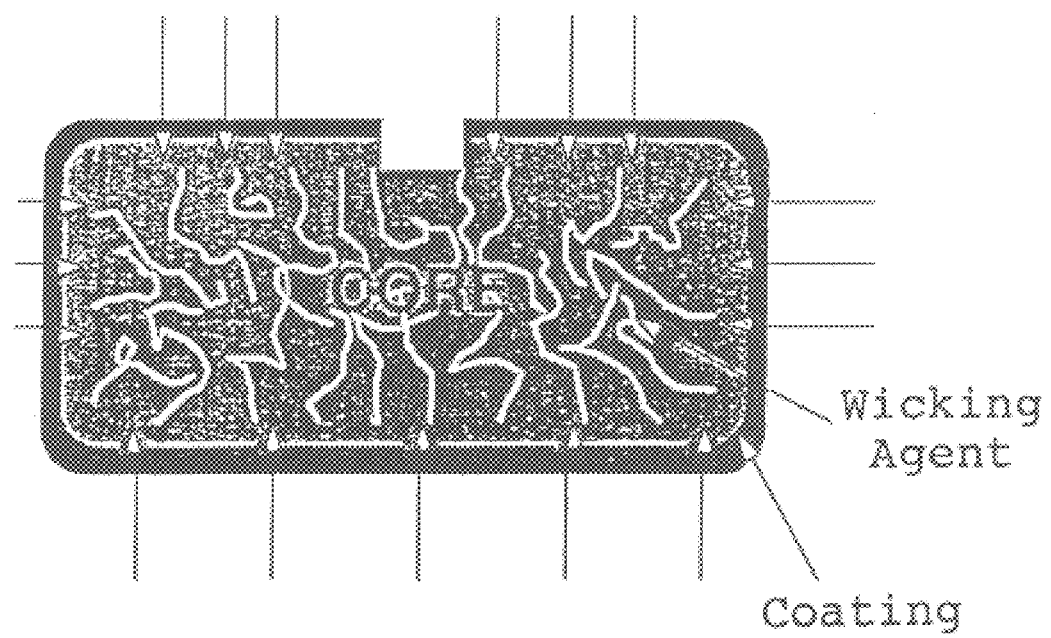
FIG. 2 schematically illustrates the osmotic dose delivery system of the present invention.

The invention will now be described in more detail with respect to numerous embodiments and examples in support thereof.

The semi-permeable wall of the elementary osmotic delivery system is composed of a polymeric material cast or sprayed onto the tablet to give a 2–15% coating weight. One example of a polymeric material includes, but is not limited to, cellulose acetate. The use of such polymeric material requires plasticizers for increased flexibility, durability, and stability. In the case of cellulose acetate, examples of suitable plasticizers are triethyl citrate (TEC), propylene glycol (PG), a mixture of TEC and PG in ratios ranging from 25% TEC plus 75% PG to 75% TEC plus 25% PG, Tween 80 or other polyoxyethylene sorbitan esters, triacetin, diethyl phthalate, polyethylene glycol, mineral oil, tributyl sebacate, and glycerol. The plasticizers are included as a weight ratio of cellulose acetate suitable for creating a semi-permeable wall to achieve retainment of the bioactive substance while permitting water permeation to the core of the tablet.

The semi-permeable wall of the tablet can contain at least one passageway communicating the contents of the core with the exterior of the device, delivering the beneficial drug through the passageways from the elementary osmotic device. The size of an individual passageway can range from 100 microns to 1000 microns, more preferred 300 to 900 microns, most preferred 500 to 850 microns. One or multiple passageways can be present to communicate the contents with the exterior of the tablet.

A wicking agent, defined as any material with the ability to draw water into the porous network of a delivery device is included in the core of this type of tablet formulation. A wicking agent can do this with or without swelling, but those used in the present invention are non-swelling wicking agents. Some materials can both wick water and swell, others can function as wicking agents only. The wicking agents are characterized by having the ability to undergo physisorption with water. Physisorption is defined as a form of adsorption in which the solvent molecules can loosely adhere to surfaces of the wicking agent via van der Waals interaction between the surface of the wicking agent and the adsorbed molecule. In the case of a drug delivery device, the adsorbed molecule is primarily water or other biological fluid which is mainly composed of water. A wicking agent that attracts water will ultimately have a volume that is essentially composed of the volume of wicking agent and the volume of water attracted to it. A material that swells will have a volume that is essentially composed of the volume of wicking/swelling agent, the volume of water attracted to it, and an additional volume created by steric and molecular forces.

The wicking agent included in the formulations described in this invention creates channels or pores in the core of the tablet. This facilitates the channeling of water molecules through the core of the tablet by physisorption. The function of the wicking agent is to carry water to surfaces inside the core of the tablet, thereby creating channels or a network of increased surface area. For the purposes of this invention, these wicking agents do not swell to any appreciable degree. For bioactive agents with low solubility in water, the wicking agent aids in the delivery of partially solubilized bioactive agent through the passageway in the semi-permeable coating. Materials suitable for acting as wicking agents include, but are not limited to, colloidal silicon dioxide, kaolin, titanium dioxide, fumed silicon dioxide, alumina, niacinamide, sodium lauryl sulfate, low molecular weight polyvinyl pyrrolidone, m-pyrol, bentonite, magnesium aluminum silicate, polyester, polyethylene. Materials particularly suitable for the purpose of this invention include the non-swellable wicking agent, examples of which are sodium lauryl sulfate, colloidal silicon dioxide, and low molecular weight polyvinylpyrrolidone.

Preferred non-swelling solubilizing agents include (i) agents that inhibit crystal formation of the pharmaceutical or otherwise acts by complexation therewith; (ii) a high HLB (hydrophilic-lipophilic balance) micelle-forming surfactant, particularly anionic surfactants; (iii) citrate esters; (iv) stearate salts; and combinations thereof, particularly combinations of complexation agents with anionic surfactants. Examples of the agents that inhibit crystal formation of the pharmaceutical or otherwise acts by complexation therewith include polyvinylpyrrolidone, polyethyleneglycol (particularly PEG 8000),α, β and δ cyclodextrins and other modified cyclodextrins, gelatin, maltodextrin, sorbitol, and polyglyceryl mixed vegetable fatty acid esters. Examples of the high HLB, micelle-forming surfactants include non-ionic and/or anionic surfactants, such as Tween 20, Tween 60 or Tween 80 Gelucire 44/14, and Labasol; polyoxyethylene or polyethylene-containing surfactants, or other long chain anionic surfactants, particularly sodium lauryl sulfate. Examples of citrate ester derivatives that are preferred are the alkyl esters, particularly triethyl citrate. Examples of stearate salts include magnesium stearate, sodium stearate, calcium stearate, and zinc stearate. Combinations of these types of non-swelling solubilizing agents are especially effective. Preferred among such types of combinations are combinations of complexation agents and anionic surfactants. Particularly preferred examples of such combinations are polyvinylpyrrolidone with sodium lauryl sulfate and polyethyleneglycol with sodium lauryl sulfate.

Lubricants are also added to assure proper tableting, and these can include, but are not limited to: magnesium stearate, calcium, stearate, zinc stearate, stearic acid, polyethylene glycol, leucine, glyceryl behenate, sodium lauryl sulfate, sodium stearyl fumarate, and hydrogenated vegetable oil. These lubricants should be present in amounts from 0.1–10% (w/w), with a preferred range of 0.3–3.0% (w/w).

Preferred lubricants for tableting include but are not limited to sodium stearyl fumarate, magnesium stearate, calcium stearate, zinc stearate, stearic acid, glycerol behenate, sodium lauryl sulfate, polyethylene glycol and hydrogenated vegetable oil. Particularly preferred lubricants are those which are soluble in water or gastric fluids or are readily emulsified. Combinations of lubricants are especially effective. Lubricant combinations which are preferred are a small amount of hydrophobic lubricant with a larger amount of soluble or emulsifiable lubricant. The rate of use for lubricants extends from 0.25 to 10.0% with a preferred range of 1 to 4%.

The delivery system of the invention can be used to provide controlled release of any of a broad variety of therapeutically active agents. Examples include the following: cough suppressants, such as dextromethorphan hydrobromide and codeine; antihistamines such as chlorpheniramine maleate, brompheniramine maleate, loratidine, astemizole, diclofenac sodium and terfenadine; decongestants such as pseudoephedrine and phenylephrine; antihypertensives such as nifedipine, verapamil, enalapril and salts thereof, metoprolol, metoprolol succinate, metoprolol fumarate, metoprolol tartarate; calcium channel blockers such as verapamil, diltiazam, nifedipine, nimodipine, felodipine, nicardipine, isradipine and amlodipine; antidiabetic agents such as glipizide and ibromectin; proton pump inhibitors such as omeprazole; H2 receptor antagonists such as cimetidine, ranitidine, famotidine, nizatidine; carbamazepine; anti-Parkinson agents such as selegiline, carbidopa/levodopa, pergolide, bromocriptine, amantadine, trihexyphenidyl HCl; antiviral agents including antiherpesvirus agents such as acyclovir, famciclovir, foscarnet, ganciclovir; antiretroviral agents such as didanosine, stavudine, zalcitabine, zidovudine; and others such as amantadine, interferon alpha, ribavirin, rimantadine; and other therapeutic agents such as cimetidine, propiomazine, phenytoin, tacrine, propiazam, proplazam. The system of the present invention is particularly applicable to therapeutic agents which are insoluble or poorly soluble in water or aqueous environments at physiological pH.

In a preferred embodiment the system of the present invention is employed for dispensing nifedipine. In such a preferred embodiment, the composition is free of agents which prevents solubilization of the nifedipine such as the Group I and Group II metals and salts thereof. In such compositions preferred osmotic agents are sugars.

In yet another aspect of the preset invention, there is provided an osmotic pharmaceutical delivery system which dispenses glipizide. The system comprises a semipermeable wall that maintains its integrity during pharmaceutical delivery, and which has at least one passage therethrough, and a composition within the wall. The composition comprises (i) glipizide; (ii) at least one non-swelling solubilizing agent which enhances the solubility of the glipizide; (iii) at least one non-swelling osmotic agent; and (iv) at least one lubricant.

In general, glipizide is present in the system in an amount of from about 0.5 wt. % to about 5.0 wt. %, preferably from about 1.0 wt. % to about 3.0 wt. %.

In one embodiment, the at least one non-swelling solubilizing agent which enhances the solubility of the glipizide is selected from the group consisting of (A) agents that inhibit crystal formation of the glipizide; (B) high HLB (hydrophilic-lipophilic balance) surfactants; (C) stearate salts; and mixtures thereof. The at least one non-swelling solubilizing agent is present in the system in an amount of from about 0.1 wt. % to about 10.0 wt. %, preferably from about 4.0 wt. % to about 6.0 wt.%.

Agents that inhibit crystal formation of the glipizide include, but are not limited to, polyvinylpyrrolidone, polyethylene glycol, cyclodextrin, gelatin, maltodextrin, sorbitol, and polyglyceryl mixed vegetable fatty acid esters.

High HLB surfactants include, but are not limited to, sodium lauryl sulfate (SLS), polysorbates such as polysorbate 20 and polysorbate 80 and polysorbate 85 (Tween), and polyglycolized glycerides and their derivatives (Gelucire and Labrasol).

Stearate salts include, but are not limited to, magnesium stearate, sodium stearate, calcium stearate, and zinc stearate.

Non-swelling osmotic agents which may be employed in the system include, but are not limited to, xylitol, mannitol, sorbitol, inositol, sucrose, lactose, dextrose, and maltodextrins. In general, the at least one non-swelling osmotic agent is present in the system in an amount of from about 60 wt. % to about 99 wt. %, preferably from about 80 wt. % to about 95 wt. %.

Lubricants which may be employed include, but are not limited to, magnesium stearate, calcium stearate, zinc stearate, stearic acid, polyethlene glycol, glyceryl behenate, sodium lauryl sulfate, sodium stearyl fumarate, and hydrogenated vegetable oil. In general, the at least one lubricant is present in the system in an amount of from about 0.25 wt. % to about 5 wt. %, preferably from about 1 wt. % to about 3 wt. %.

The semi-permeable wall is comprised of a polymeric material that is cast or sprayed onto the tablet. In general, the wall is present in an amount of from about 2 wt. % to about 15 wt. % of the total weight of the composition. Polymeric materials from which the wall may be formed include, but are not limited to, cellulose acetate. The wall also may further include plasticizers for increased flexibility, durability, and stability. Such plasticizers include, but are not limited to, triethyl citrate (TEC), propylene glycol (PG) or mixtures thereof in ratios of TEC to PG ranging from 25:75 to 75:25; Tween 80 or other polyoxyethylene sorbitan esters, triacetin, diethyl phthalate, polyethylene glycol, mineral oil, tributyl sebacate, and glycerol. The plasticizers may aid in retaining the glipizide while permitting the permeation of water to the core of the tablet.

The semi-permeable wall also includes at least one opening to provide for the delivery of the glipizide. In general, the at least one opening(s) has a diameter of from about 100 microns to about 1,000 microns, preferably from about 200 microns to about 800 microns, more preferably from about 250 microns to about 500 microns. The at least one opening(s) is (are) formed in general by laser drilling or otherwise boring or creating a passageway through the semi-permeable film in order to conduct the solubilized glipizide into the exterior fluid environment.

The system may further include an overcoating which covers the semi-permeable wall. The overcoating can be formulated to provide light protection, atmospheric humidity protection, and a brief lag time in the release of the glipizide from the osmotic delivery system. The overcoating may comprise a mixture of a sustained release coating polymer, such as ethylcellulose, and a water soluble coating polymer such as hydroxypropylcellulose. The overcoating is cast or sprayed onto the tablets with a 2% to 15% weight gain. The ratio of sustained release polymer to water soluble polymer is varied to achieve the desired lag time and humidity protection. The ratio of sustained release polymer to water soluble polymer may vary from 9:1 to 1:9, preferably from 1:1 to 9:1, and more preferably from 3:1 to 5:1.

The components of the glipizide delivery system of the present invention can be used to provide controlled release of the glipizide. In a preferred embodiment, the core composition including the glipizde is free of agents that prevent the solubilization of the glipizide when combined to form the finished delivery system. This is done by evaluating the solubility of each component and their combinations using standard solubility testing techniques. A preferred technique consists of creating a saturated solution of glipizide in the presence of the desired component or mixture of components, and quantifying the amount of solubilized glipzide in the filtered supernatant with a validated high pressure liquid chromatograph. Further, multicomponent solubilization systems are optimized to maximize the solubility of glipizide using statistical designs of experiments.

The core composition containing the glipizide may be prepared for tablet compression by any of several standard techniques known to those skilled in the art. Such methods include, but are not limited to, direct compression, roller compaction, wet granulation with aqueous or solvent based binders, slugging, and granulation such as high shear granulation and fluid bed granulation. Granulation is preferred. Once granulation is achieved, the granules are lubricated by adding magnesium stearate or other suitable tablet lubricating agents, followed by dry blending in a tumble blender or other suitable mixer to effect adequate distribution of the tablet lubrication agents. The lubricated granules then are compressed on a rotary tablet press. The tablets must have sufficient hardness and friability to allow for coating.

The core tablets then are coated with a semipermeable film which forms the semi-permeable wall hereinabove described. Preferred methods of coating includes, but are not limited to, pan coating and wurster column coating. The coating solution is prepared and applied at a rate in order to provide a smooth and even coverage of the entire surface area of the tablet. The percent weight gain of the tablet as a result of application of the coating will vary, depending upon the size and shape of the tablet that is coated, but generally is from about 2% to about 15%.

A passageway then is formed in the semi-permeable film coated tablets by laser drilling, mechanical drilling, or other drilling methods known to those skilled in the art. Other methods of forming a passageway or a multiplicity of passageways also are known to those skilled in the art.

When an overcoating is applied to the semi-permeable film coated tablet, the overcoating preferably is applied in a pan coater or a wurster column coater. The coating solution is applied in order to provide a smooth and even coverage over the entire surface area of the tablets. The coating solution may be an aqueous solution or a solvent based solution. The percent weight gain provided by the overcoating will vary, depending upon the size and shape of the tablets, but generally is from about 2% to 15%.

The invention now will be described with respect to the following examples; however, the scope of the present invention is not intended to be limited thereby.

EXAMPLE 1

Nifedipine Granulation/Tableting/Coating (TEC) or another suitable wetting agent is added to enough water to produce a good dispersion which will atomize and pump well. Add between 50 to 100% of the PEG 8000. Next add between 50 to 100% of the nifedipine to the dispersion. Finally add between 25 to 75% of the Cab-o-Sil® to the binder dispersion. Mix for ~20 minutes before spraying. Also, other ingredients can be added to or removed from the dispersion as necessary. A dispersion is also not necessary, the binder may be a solution of PVP, PEG, sugar or other binder. The solution may be aqueous or organic. In some cases, a hot melt method of granulating may be preferred. In this case, the binder may be a molten wax, wax mixture or other material.

Charge a fluid bed bowl with osmagents (xylitol, sorbitol lactose, fructose, inositol, etc.). Add between 50 to 100% of the SLS, add the remaining PEG 8000, and add between 50–100% of the PVP K-25, add all or the remaining amount of Nitedipine and other ingredients as required.

Spray the dispersion onto the powder bed with a spray rate of 20–50 g/min which will produce granules of an adequate size for tableting. (Spray rate will vary with batch size.) Inlet air flow rate and temperature are adjusted to keep powder bed from over-granulating or becoming overly wet. (Typical range 100–250 CMH and 40–60° C., depending on batch size.)

Discharge granulation and add remaining sodium lauryl sulfate (SLS), polyvinyl pyrrolidone (PVP K-25), osmagents, polyethylene glycol (PEG), nifedipine and Cab-o-Sil® (colloidal silicon dioxide; Cabot Corporation) and mix in a V-blender or appropriate mixer for 2–5 minutes or as necessary. Add suitable lubricant such as Magnesium Stearate (approximately 0.5–1.5%) and blend 2–5 minutes or as necessary.

Discharge final blend from mixer and tablet on suitable tablet press. Coat tablets in pan coater or fluid bed dryer with spray rate of 30–100 g/min or higher (depending on batch size). The coating solution is prepared by dissolving ~5% cellulose Acetate, NF (National Formulary) in Acetone or other suitable solvent then adding 25–45% plasticizers such as TEC or PG or mixture thereof.

Process may also be done by direct compression, high shear granulation, dry compression or slugging.

In some cases it may be desirable to modify the solubility characteristics of the osmagents, solubilizers, granulation or other ingredient to achieve a desired release profile.

One method for modifying the release profile is to use a hydrophobic coating method. Initially, all ingredients could be granulated together with a 0–20% PVP K 25 or PEG 8000 or other binder aqueous or organic solution to ensure that drug, sugars, and solubilizers are evenly distributed throughout the granules. Following this procedure, a coating agent such as hydrogenated castor oil, hydrogenated vegetable oil, type I, ethyl cellulose, glyceryl monostearate, Gelucire® or carnauba wax at 1–20% of the total formulation weight could be applied to 5–50% of the total granulation. The coating agent may be applied in a fluid bed by top spray, wurtser column coating, or rotor application; a pan coater equipped with a screen for coating granules may also be utilized. The hydrophobic agent could be applied in a melted state or dissolved in a suitable solvent in which it would be sprayed onto the granules. Both parts of the granulation, immediate and sustained release, could then be blended thoroughly by using a V-Blender before tableting.

Alternatively, the method presented above may be applied to a component or combination of components of the formulation. One or more of the osmagents may be granulated alone or in combination with other osmagents, solubilizers or other components of the core. These granules may then be coated alone or in combination with any other component of the core with the materials and methods described above. The coated granules can then be added to the rest of formulation by dry blending, or they may actually be granulated with the remainder of the formulation.

Alternatively, a hydrophobic granulation method may be utilized. In this method powdered wax is mixed together with the portion of the granulation to be coated (in the same percentage ranges already stated). Non-powdered wax may be utilized by milling the wax to a fine particle size. Wax mixtures may be formed by melting the wax, adding the desired component, allowing the mixture to congeal and then screening or milling the wax mixture to a fine particle size. The powdered wax or wax mixture is then added to the fluid bed with the portion of the granulation to be coated. The materials are granulated by increasing and controlling the inlet temperatures of the fluid bed (inlet temperature ~60–80° C., outlet temperature ~40–60° C.), to cause the melting/congealing steps involved in the granulation process. In other instances a jacketed device could be used to granulate. Here, however, the temperature ranges would apply to the substance used in heating and cooling the device, such as steam, hot oil or water.

For sustained release agents which are not waxes, the granulation process can be carried out utilizing standard granulation techniques such as aqueous moist granulation or solvent granulation (in the same percentage ranges already stated). The sustained release agent may be dissolved or suspended in the granulating fluid or it may be dispersed with the powders to be granulated. The granules are formed and dried and finally added to the remainder of the formulation.

Again, the above granulation techniques may be applied to a portion of the entire formulation or any component or mixture of components in the formulation. The sustained release granules may then be combined with the remainder of the formulation by techniques previously discussed.

Finally, a matrix technique may be utilized. This technique involves adding a powdered wax at 5–30% of the total formulation weight, such as hydrogenated castor oil, glyceryl palmitostearate, glyceryl behenate, Gelucire®, PEG 8000 or any other non-swellable matrix forming agent known to one skilled in the art to the formulation. The wax may be granulated with any component or combination of components of the formulation with a 0–20% PVP K25 or PEG 8000 or other binder solution, or a roller compaction or slugging method may be used in the formation of the granules. The granules are then added to the remainder of the formulation using the methods stated earlier.

The modified release osmagents, solubilizers or granulation may then be tableted after addition of a suitable lubricant. A single layer tablet would have all components of the formulation blended together and compressed. One or more holes may be provided to give the proper release. One or more holes may be provided on the tablet. It may be beneficial for a tablet to have a hole on both sides of the tablet so that the optimum release rate is achieved. One or more holes may be provided to achieve the desired release characteristics.

It is possible that any of the previously discussed excipients in combination with the tablet core may lower the melting point. The temperatures that the tablet should be exposed to in an aqueous color coating process may be extreme enough (~60° C.) to partially melt the core and change the physico-chemical behavior of the tablet in dissolution or stability. To avoid this change, a solvent-based color coat was formulated at Shire Laboratories Inc., consisting of a 1:1 mixture of hydroxypropyl cellulose and HPMC, and 1% of a colored aluminum lake dispersed in a 70:30 IPA:Water solution. Because the color coat is solvent-based, the temperature that the tablets will be exposed to in the coating process is significantly lower (~35–40° C.).

A one to two hour delay before the onset of dissolution may be beneficial. In order to provide this lag time a seal coat may be added to the tablet. The seal coat should provide a water impermeable barrier for no longer than two hours. Some polymers which would provide this type of coating include ethylcellulose, shellac, Eudragit RS. Other ingredients may be added to the polymers in order to modify the coating to achieve the desired lag time. A 1–10% weight gain should be applied to the tablets. The coating is applied as an aqueous or organic solvent solution or dispersion. The coating is typically applied in a coating pan or fluid bed equipped with a wurster column.

EXAMPLE 2

Nifedipine Formulations

The following are examples of formulations of the single, homogeneous composition within the tablet wall of the dosage form of the invention.

TABLE 1

| Ingredients | 1A | 1B | 1C | 1D | 1E | 1F | 1G | 1H |
|---|---|---|---|---|---|---|---|---|
| Fructose |  | 43.5 | 21.5 | 49.6 | 44.5 | 37.2 | 20.5 | 18.5 |
| Lactose 315 | 17 | 18 | 17 | 17 | 17 | 32 | 17 | 17 |
| Sorbitol | 43.5 |  | 21 |  |  |  | 21 | 19 |
| PVPK25 | 15 | 15 | 15 | 12.7 | 15 | 12.5 | 15 | 10 |
| PEG8000 | 10 (5*) | 10 (5*) | 10 (5*) | 8.5 (4.2*) | 10 (5*) | 8.4 (4.2*) | 10 (5*) | 20 (10*) |
| TEC | 1* | 1* | 1* | 1.7* | 1* | 0.84* | 1* | 1* |
| SLS | 3 | 3 | 3 | 3 | 3 (1.5*) | 1.95 (1.25*) | 3 | 3 |
| Cab-o-Sil ® | 2.0 (0.5*) | 1.0 (0.5*) | 1 (0.5*) | 0.92 (0.42) | 1 (0.5*) | 1.1 (0.4*) | 1 (0.5*) | 0.5 |
| Nifedipine | 8* | 8* | 8* | 6.8* | 8* | 6.7 | 8* | 8* |
| Mg Stearate | 0.5 | 0.5 | 0.5 | 0.5 | 0.5 | 0.5 | 0.5 | 3 |
| K Sorbate |  |  |  |  |  |  | 3 |  |
| Total | 100 | 100 | 100 | 100 | 100 | 100 | 100 | 100 |

*Indicates in dispersion

TABLE 2

| Ingredients | 2A | 2B | 2C | 2D | 2E |
|---|---|---|---|---|---|
| Fructose | | | | | |
| Lactose 315 | | | | | |
| Sorbitol | 15.5 | 15.5 | 5.5 | 23.25 | 12.5 |
| Xylitol | 23.25 | 23.25 | 23.25 | 15.5 | 6.5 |
| Mannitol | | | | | |
| PVPK-12PF | | | | | |
| PVP-K25 | 35 | 35 | 35 | 35 | 50 |
| PEG8000 | 10 (5*) | 10* | 20 (10*) | 10 (5*) | 10 (5*) |
| SLS | 5 | 5 | 5 | 5 | 10 |
| Cab-o-Sil ® | 1 (0.5*) | 1 (0.5*) | 1 (0.5) | 1 (0.5*) | |
| Nifedipine | 8.25* | 8.25* | 8.25 | 8.25* | 10 |
| TEC | 1* | 1* | 1* | 1* | |
| Mg Stearate | 1 | 1 | 1 | 1 | 1 |
| Total | 100 | 100 | 100 | 100 | 100 |

*Indicates in dispersion

TABLE 3

| Ingredients | 3A | 3B | 3C | 3D | 3E | 3F | 3G | 3H |
|---|---|---|---|---|---|---|---|---|
| Fructose | 21.5 | 20.5 | 19.5 | 16.5 | 18.5 | 17.5 | 17.5 | 16.5 |
| Lactose 315 | 17 | 17 | 17 | 17 | 17 | 17 | 17 | 14.5 |
| Sorbitol | 23 | 21 | 23 | 21 | 21 | 20 | 20 | 18.5 |
| PVPK25 | 15 | 15 | 15 | 15 | 15 | 15 | 15 | 15 |
| PEG8000 | 10 (5*) | 10 (5*) | 10 (5*) | 10 (5*) | 10 (5*) | 10 (5*) | 10 (5*) | 10 (5*) |
| TEC | 1* | 1* | 1* | 1* | 1* | | 1* | 1* |
| SLS | 3 | 3 | 5 | 5 | 3 | 5 | 5 | 5 |
| Cab-o-Sil ® | 1 (0.5*) | 1 (0.5*) | 1 (0.5*) | 1 (0.5*) | 1 (0.5*) | 1 (0.5*) | 1(0.5*) | 1(0.5*) |
| Nifedipine | 8* | 8* | 8* | 8* | 8* | 8* | 8* | 8* |
| Mg Stearate | 0.5 | 0.5 | 0.5 | 0.5 | 0.5 | 0.5 | 0.5 | 0.5 |
| K Sorbate | | 3 | | 5 | 5 | | | |
| Glycerol | | | | | | 5 | | |
| Cremophor EL** | | | | | | | 5 | |
| Inositol | | | | | | | | 10* |
| Total | 100 | 100 | 100 | 100 | 100 | 100 | 100 | 100 |

*Indicates in dispersion
**Polyethylene glycol castor oil derivative (other suitable derivatives of castor oil are disclosed by the International Cosmetic Ingredient Dictionary (5th Ed.), Cosmetic Fragrance and Toiletry Association, Washington, D.C. (1993), e.g. at pages 479-481)

TABLE 4

| Ingredients | 4A | 4B | 4C | 4D | 4E | 4F | 4G | 4H |
|---|---|---|---|---|---|---|---|---|
| Fructose | 13 | 13 | 4.5 | 17.5 | 18.5 | 15.25 | 15.675 | 15.675 |
| Lactose 315 | 10.5 | 10.5 | 4 | 17 | 17.5 | 30 | 16.15 | 16.15 |
| Sorbitol | 16 | 16 | 6 | 20 | 22 | | 19.95 | 19.95 |
| PVPK25 | 35 | 15 | 35 | 15 | 15 | 15 | 14.25 | 14.25 |
| PEG8000 | 10 (5*) | 35 (5*) | 35 (5*) | 10 (5*) | 10 (5*) | 10 | 9.5 (4.75*) | 9.5 (4.75*) |
| TEC | 1* | 1* | 1* | 6* | | | 0.95* | 0.95* |
| SLS | 5 | 5 | 5 | 5 | 5 | 5 | 5 | 5 |
| Cab-o-Sil ® | 1. (0.5*) | 1.0 (0.5*) | 1.0 (0.5*) | 1.0 (0.5*) | 1.0 (0.5*) | 1 | .975 (0.475*) | .975 (0.475*) |
| Nifedipine | 8* | 8* | 8* | 8* | 8* | 8.25 | 7.6* | 7.6* |
| Mg Stearate | 0.5 | 0.5 | 0.5 | 0.5 | 0.5 | 0.5 | 0.5 | 0.5 |
| K Sorbate | | | | | | | 4.75 | 4.75 |
| Glycerol | | | | | 2.5 | | | |
| CremophorEL | | | | | | 10 | | |
| Inositol | | | | | | | 5 | |
| Calcium Sulfate | | | | | | | | 5 |
| Total | 100 | 100 | 100 | 100 | 100 | 100 | 100 | 100 |

*Indicates in dispersion

TABLE 5

| Ingredients | 5A | 5B | 5C | 5D | 5E | 5F | 5G | 5H |
|---|---|---|---|---|---|---|---|---|
| Xylitol | 15.5 | 5 | 32.5 | | 31.5 | 24.0 | 16.9 | 20 |
| Sorbitol | 15.0 | 5 | | 17.5 | 15.5 | 15.5 | 15 | 18.75 |
| Fructose | | 7.5 | | 17.5 | | | | |
| Lactose | | 5 | | | | | | |
| PEG 8000 | 10 | 10 | 20 | 10 | | 10 (5*) | | 10 |
| PVP K-25 | 35 | 35 | 15 | 15 | 35 | 35 | 50 | 35(5*) |
| TEC | 1 | 1 | 1 | 1.0 | 1* | 1* | 1* | 1* |
| Cab-o-Sil ® | 1.0 | 1 | 1 | | 1 (0.5) | 2 (1*) | 1 (0.5*) | 1 (0.5*) |
| Nifedipine | 17 | 25 | 25 | 50.0 | 10 | 10 | 10.1 | 8.25 |
| Mg Stearate | 0.5 | 0.5 | 0.5 | 0.5 | 1 | 1 | 1 | 1 |

TABLE 5-continued

| Ingredients | 5A | 5B | 5C | 5D | 5E | 5F | 5G | 5H |
|---|---|---|---|---|---|---|---|---|
| SLS | 5.0 | 5 | 5 | 3 | | 5 | 5 | 5 |
| K Sorbate | | | | 3 | | | | |
| Total | 100 | 100 | 100 | 100 | 100 | 100 | 100 | 100 |

*Indicates in dispersion

TABLE 6

Nifedipine Formulations

| | 6A | 6B | 6C | 6D | 6E | 6F | 6G | 6H |
|---|---|---|---|---|---|---|---|---|
| Xylitol | 27.5 | 27.5 | 25.5 | 30.8 | 28.5 | 32.5 | 34.5 | 25.5 |
| Sorbitol | 25 | 25 | 26 | 28.5 | 29 | 30 | 30 | 26 |
| SLS | 5 | 5 | 4.5 | 4.8 | 5 | 5 | 5 | 4.5 |
| PVP K25 | 15 (3*) | 15 (3*) | 13.5 (2.7*) | 14.2 (2.8*) | 15 (3*) | 15 (3*) | 5 | 13.5 |
| Nifedipine | 15 | 15 | 18 | 14.2 | 20 | 15 | 17.5 | 18 |
| Stearic Acid | 1 | 11 | 1 | 1 | 1 | 1 | 2 | 1 |
| Mag. Stearate | 1 | 1 | 1 | 1 | 1 | 1 | 0.5 | 1 |
| Cab-o-sil ® | 0.5 | 0.5 | 0.5 | 0.5 | 0.5 | 0.5 | 0.5 | 0.5 |
| Glycerol Behenate | 10 | | | | | | | |
| Stearic Acid (Binder) | | | | | | | 5.0 | |
| Stearic Acid Coated Xylitol | | | 10 | 5 | | | | |
| Stearic Acid Coated 6E | | | | | | | | 10 |

EXAMPLE 3

Comparative Percentage of Nifedipine Release

This example reports experiments which compared the percentage of nifedipine released by certain of the above formulations in dose delivery forms of the invention as compared to Procardia XL®(Pfizer, Inc.; 30 mg).

Materials and Methods

Dose delivery forms of the invention are placed in a Vankel Dissolution Apparatus containing simulated gastric fluid without enzymes and dissoluted for 20 to 24 hours. Samples of the dissolution media are taken periodically and analyzed by high performance liquid chromatography for nifedipine concentration. The calculated percent release is plotted versus time. Dose delivery forms of the invention and procardia XL tablets are tested in the same manner to produce effective comparisons.

Results

Figure 3:
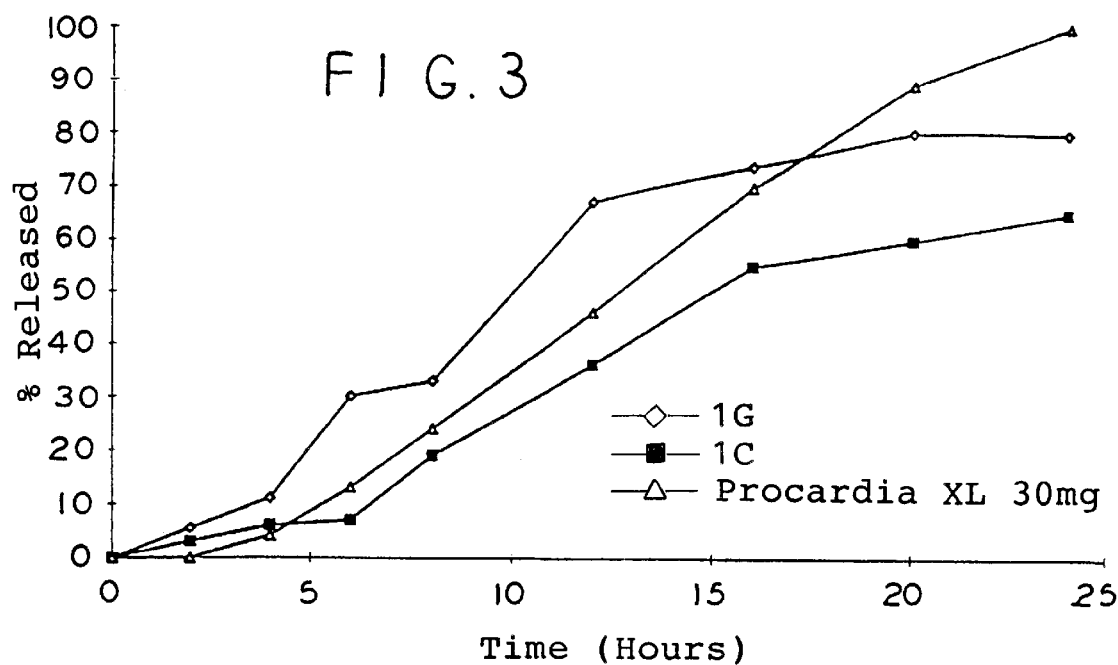
FIG. 3 diagrammatically shows the percent of nifedipine released by dosage forms of the invention containing formulations 1G (30 mg); 1C (30 mg); as shown on Table 1 as compared to Procardia XL®(Pfizer, Inc.; 30 mg).

FIG. 3 diagrammatically shows the percent of nifedipine released by dosage forms of the invention containing formulations 1G (30 mg); 1C (30 mg); as shown on Table 1 as compared to Procardia XL®(Pfizer, Inc.; 30 mg).

Figure 4:
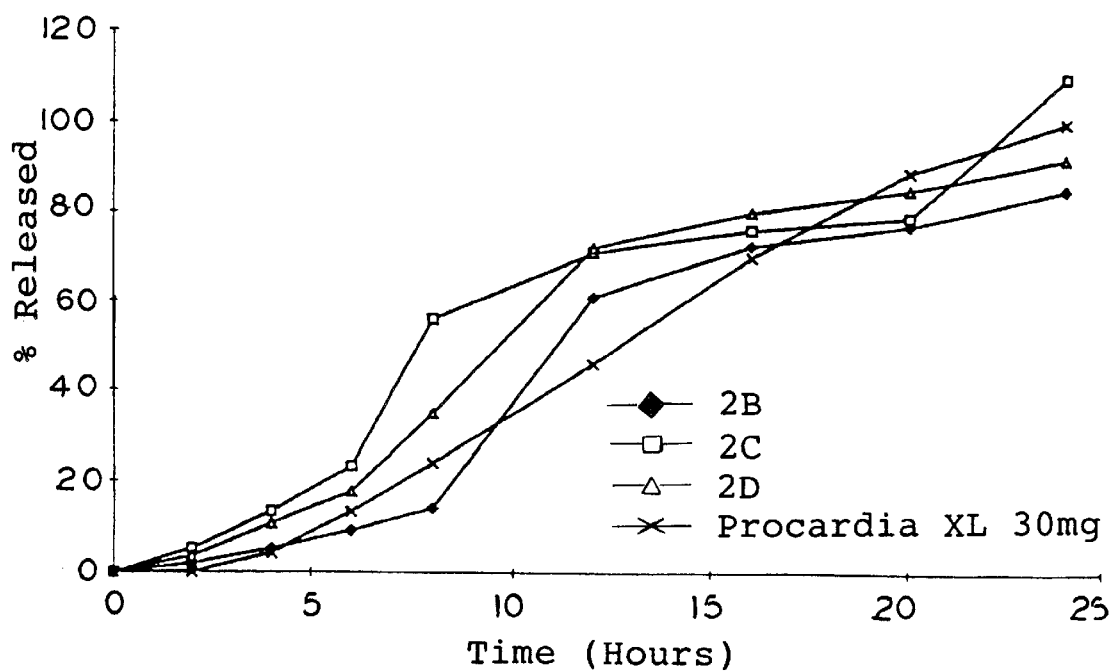
FIG. 4 diagrammatically shows the percent of nifedipine released by dosage forms of the invention containing formulations 2B (47 mg); 2C (47 mg); and 2D (47 mg) as shown on Table 2 as compared to Procardia XL®(Pfizer, Inc.; 30 mg).

FIG. 4 diagrammatically shows the percent of nifedipine released by dosage forms of the invention containing formulations 2B (47 mg); 2C (47 mg); and 2D (47 mg) as shown on Table 2 as compared to Procardia XL®((Pfizer, Inc.; 30 mg).

FIG. 5 diagrammatically shows the percent of nifedipine released by dosage forms of the invention containing formulations 3C (30 mg); 3H (30 mg); as shown on Table 3 as compared to Procardia XL®((Pfizer, Inc.; 30 mg).

FIG. 6 diagrammatically shows the percent of nifedipine released by forms of the invention containing formulations 4H (30 mg); 4C (90 mg); as shown on Table 4 as compared to Procardia XL®(Pfizer, Inc.; 30 mg).

Figure 7:
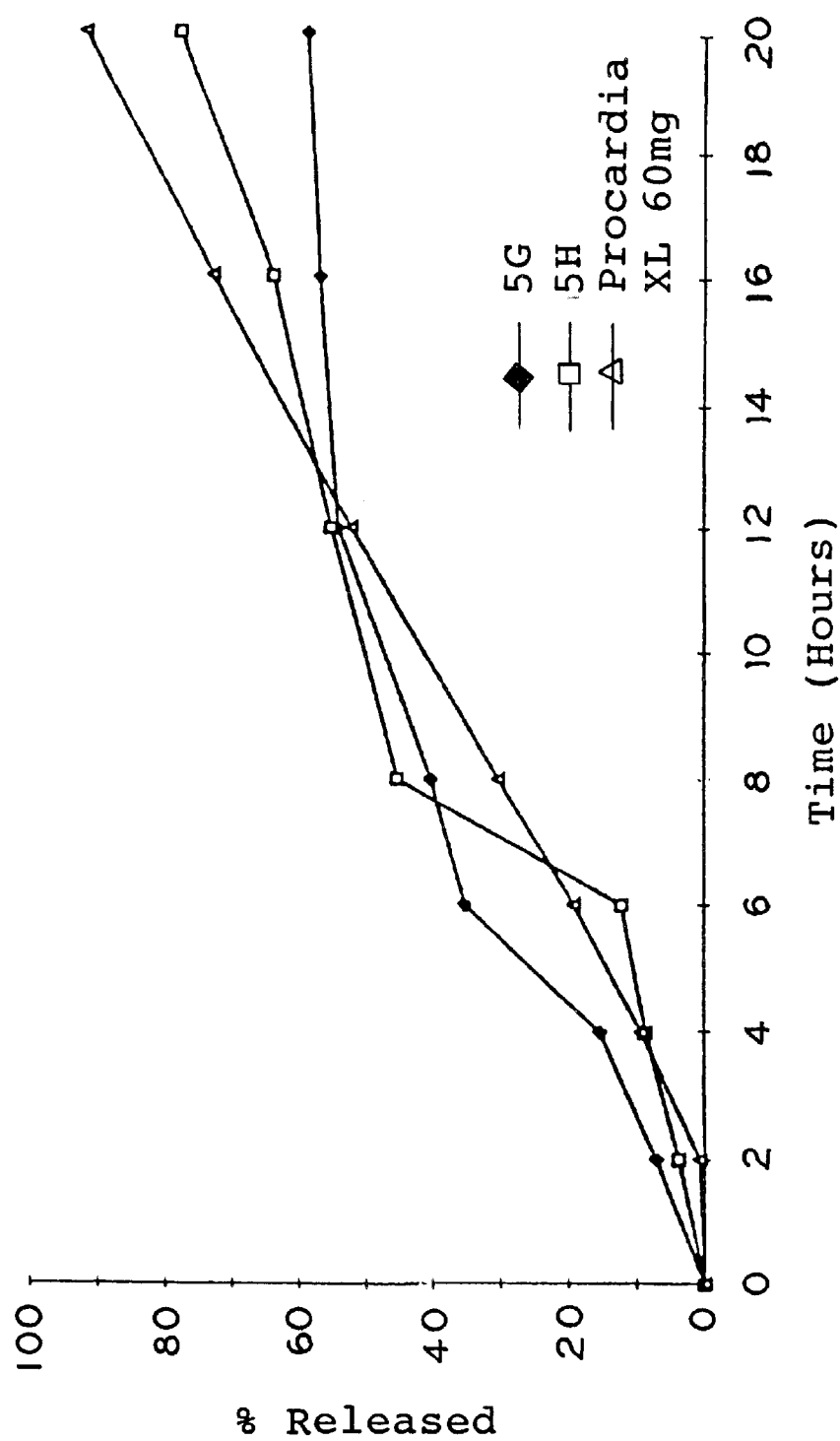
FIG. 7 diagrammatically shows the percent of nifedipine released by forms of the invention containing formulations 5G (60 mg); 5H (60 mg); as shown on Table 5 as compared to Procardia XL®(Pfizer, Inc.; 60 mg).

FIG. 7 diagrammatically shows the percent of nifedipine released by forms of the invention containing formulations 5G (60 mg); 5H (60 mg); as shown on Table 5 as compared to Procardia XL®(Pfizer, Inc.; 60 mg).

Figure 8:
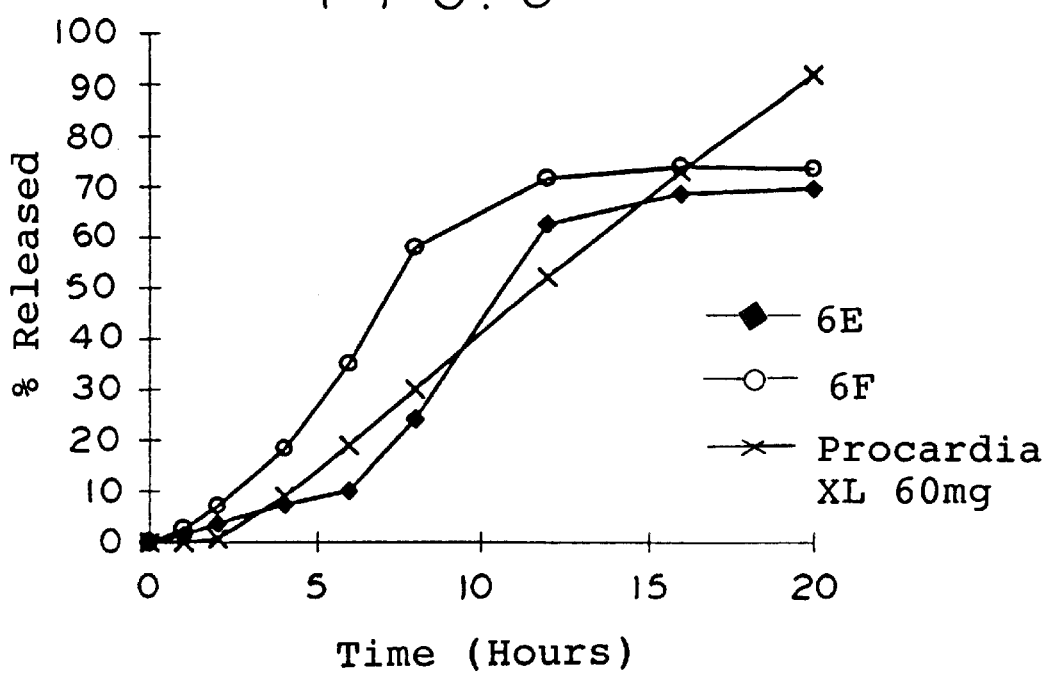
FIG. 8 diagrammatically shows the percent of nifedipine released by forms of the invention containing formulations 6E (60 mg); 6F (60 mg); as shown on Table 6 as compared to Procardia XL®(Pfizer, Inc., New York; 60 mg).

FIG. 8 diagrammatically shows the percent of nifedipine released by forms of the invention containing formulations 6E (60 mg); 6F (60 mg); as shown on Table 6 as compared to Procardia XL®(Pfizer, Inc., New York; 60 mg).

Figure 9:
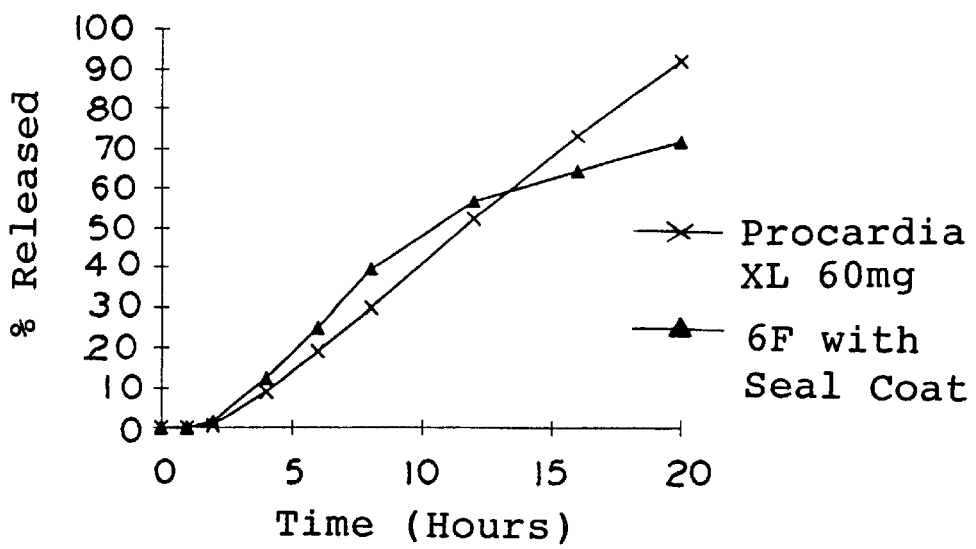
FIG. 9 diagrammatically shows the percent of nifedipine released by forms of the invention containing formulation 6F (60 mg) with a 1% ethylcellulose seal coat as shown on Table 6 as compared to Procardia XL®((Pfizer, Inc., New York; 60 mg).

FIG. 9 diagrammatically shows the percent of nifedipine released by forms of the invention containing formulation 6F (60 mg) with a 1% ethylcellulose seal coat as shown on Table 6 as compared to Procardia XL®(Pfizer, Inc., New York; 60 mg).

EXAMPLE 4

Powdered xylitol, fine granular maltodextrin, micronized glipizide, and sodium lauryl sulfate in a 40:52.5:2.5:5 ratio were added to a high shear granulation bowl and mixed for 20 minutes. Water was added until a granulation was formed. The wet granulation mass was placed quickly in a hot air oven at 60° C. to dry overnight. The next day the dried granules were passed through an 18 mesh screen and the overs were discarded. The granulation was lubricated with 0.5% magnesium stearate by dry blending in a V-blender for 3 minutes. The lubricated granulation then was compressed into tablets containing 10 mg of glipizide.

Figure 10:
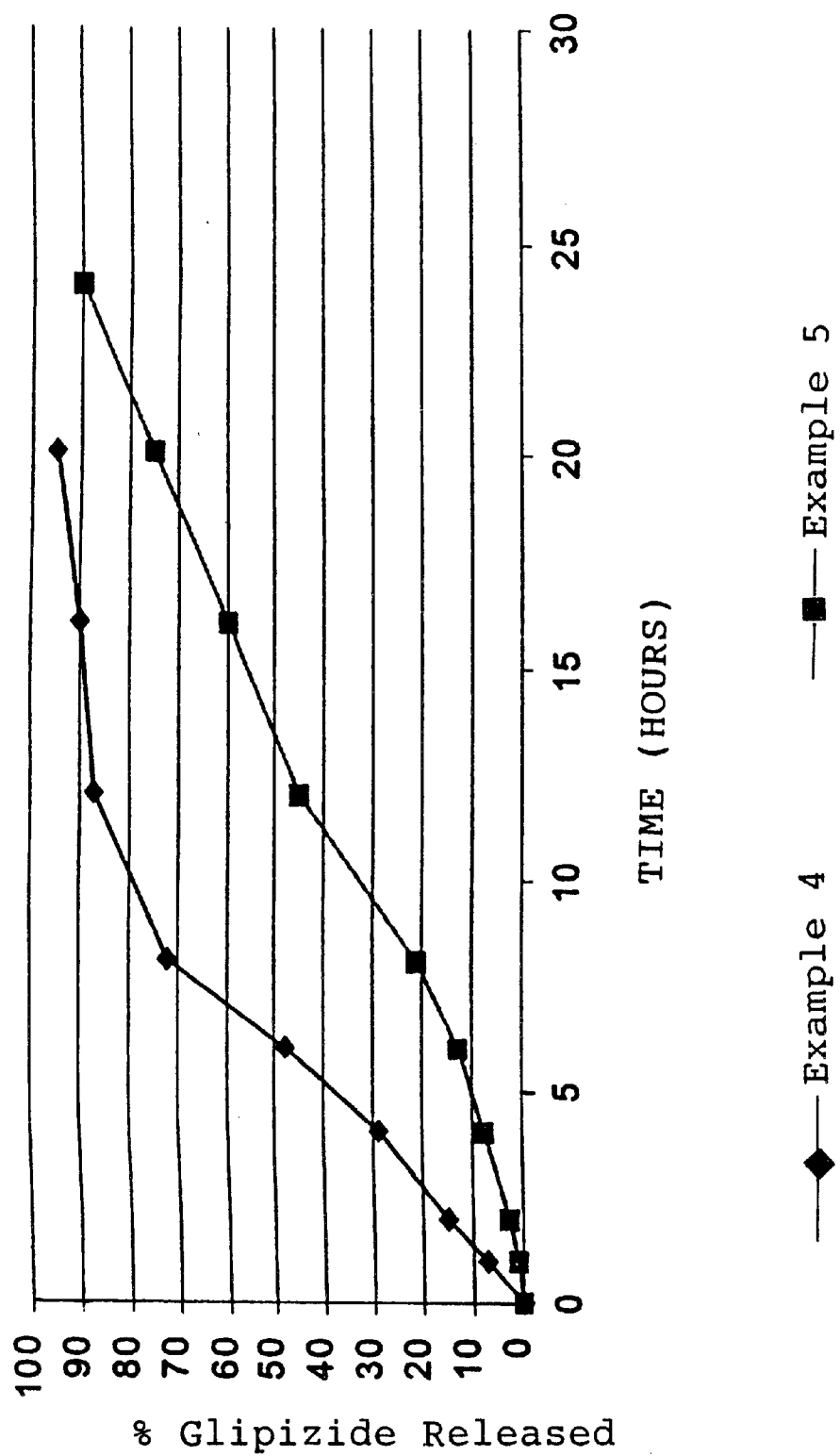
FIG. 10 is a graph showing (i) the dissolution profile showing the amount of glipizide released by tablets of the invention in which the core formulation contains granules of glipizide formed by a wet granulation method, and (ii) the dissolution profile showing the amount of glipizide released by tablets of the invention in which the core formulation contains granules of glipizide formed by a dry granulation method.

A cellulose acetate coating solution for applying the semipermeable film coating was prepared. In order to prepare the coating solution, 5% cellulose acetate was dissolved in 93.75% acetone once the cellulose acetate has dissolved, 1.25% TEC was added to the mixture to plasticize the film. The tablets then were coated with a 2.5% wt./wt. semipermeable film coating in a pancoater or other suitable coating device. The tablets then were laser drilled on one side with 200 µ radius hole. The laser drilled tablets were tested in a USP dissolution apparatus and observed to have a 12 to 16 hour dissolution profile, as shown in FIG. 10.

EXAMPLE 5

Granular xylitol, granular maltodextrin, micronized glipizide, and sodium lauryl sulfate in a 40:52.5:2.5:5 ratio were added to a V-blender and dry mixed for 10 minutes.

The dry blend was lubricated with 0.5% magnesium stearate by blending in a V-blender for 3 minutes. The lubricated direct compression blend was compressed into tablets containing 10 mg of glipizide. A cellulose acetate coating solution was prepared for applying the semi-permeable film coating. In order to prepare the coating solution, 5% cellulose acetate was dissolved in acetone. Once the cellulose acetate has dissolved, 1.25% TEC was added to the mixture to plasticize the film. The tablets then were coated with a 2.5% wt./wt. semi-permeable film coating in a rotating collander coater. The tablets then were drilled on one side with a 200 $\mu$ radius hole. The laser drilled tablets were tested in a USP dissolution apparatus and observed to have a prolonged dissolution profile as shown in FIG. 10.

The disclosures of all patents and publications (including published patent applications) are herein incorporated by reference to the same extent as if each patent and publication were individually incorporated by reference.

It is to be understood, however, that the scope of the present invention is not to be limited to the specific embodiments described above. The invention may be practiced other than as particularly described and still be written the scope of the accompanying claims.

What is claimed is:

1. A method of preparing an osmotic pharmaceutical delivery system, comprising:
   (a) adding water to a composition comprising (i) a pharmaceutical agent that has a limited solubility in water or physiological environments; (ii) at least one non-swelling solubilizing agent which enhances the solubility of said pharmaceutical agent; and (iii) at least one non-swelling osmotic agent, wherein said composition is free of an agent that provides a physical force other than by osmotic pressure for delivering the pharmaceutical agent whereby the pharmaceutical agent is delivered through the passageway by osmosis rather than by another force, to provide said composition as a wet granulation mass;
   (b) drying said wet granulation mass to provide dry granules including components (i), (ii), and (iii) hereinabove;
   (c) compressing said granules into at least one tablet; and
   (d) coating each of said at least one tablet(s) with a semipermeable wall that maintains its integrity during pharmaceutical delivery; and
   (e) providing at least one passage through said semipermeable wall.

2. The method of claim 1 wherein said at least one non-swelling solubilizing agent is selected from the group consisting of (i) agents that inhibit crystal formation of the pharmaceutical; (ii) a surfactant; (iii) citrate esters; and (iv) combinations thereof.

3. The method of claim 2 wherein said non-swelling solubilizing agent comprises the combination of at least one agent that inhibits crystal formation of the pharmaceutical with at least one surfactant.

4. The method of claim 1 wherein said semipermeable wall comprises cellulose acetate and triethyl citrate.

5. The method of claim 1 wherein said at least one solubilizing agent is selected from the group consisting of sodium lauryl sulfate and a low molecular weight polyvinylpyrrolidone, and combinations thereof.

6. The method of claim 1 wherein the pharmaceutical agent has limited aqueous solubility at physiological pH.

7. The method of claim 6 wherein the pharmaceutical agent is nifedipine.

8. The method of claim 1 wherein the composition within said wall further comprises a lubricant.

9. The method of claim 1 wherein the at least one non-swelling osmotic agent is a sugar.

10. The method of claim 9 wherein the sugar has no more than ten rings.

11. The method of claim 10 wherein the sugar has no more than five rings.

12. The method of claim 11 wherein the sugar is selected from the group consisting of monosaccharides, disaccharides, and trisaccharides.

13. The method of claim 11 wherein the sugar is selected from the group consisting of fructose, lactose, xylitol, inositol, and sorbitol.

14. The method of claim 1 wherein said pharmaceutical agent is glipizide.

15. The method of claim 14 wherein (i) the pharmaceutical agent is glipizide; (ii) the at least one non-swelling solubilizing agent is sodium lauryl sulfate; and (iii) the at least one non-swelling osmotic agent comprises at least one sugar.

* * * * *